(12) United States Patent
Barbash et al.

(10) Patent No.: US 11,830,192 B2
(45) Date of Patent: Nov. 28, 2023

(54) SYSTEM AND METHOD FOR REGION DETECTION IN TISSUE SECTIONS USING IMAGE REGISTRATION

(71) Applicant: The Joan and Irwin Jacobs Technion-Cornell Institute, New York, NY (US)

(72) Inventors: Shahar Barbash, New York, NY (US); Nadav Yayon, Jerusalem (IL)

(73) Assignee: THE JOAN AND IRWIN JACOBS TECHNION-CORNELL INSTITUTE, New York, NY (US)

( * ) Notice: Subject to any disclaimer, the term of this patent is extended or adjusted under 35 U.S.C. 154(b) by 0 days.

(21) Appl. No.: 16/928,685

(22) Filed: Jul. 14, 2020

(65) Prior Publication Data

US 2021/0035297 A1    Feb. 4, 2021

Related U.S. Application Data

(60) Provisional application No. 62/880,787, filed on Jul. 31, 2019.

(51) Int. Cl.
*G06T 7/00* (2017.01)
*G06T 7/33* (2017.01)
(Continued)

(52) U.S. Cl.
CPC ............ *G06T 7/0014* (2013.01); *G06T 7/337* (2017.01); *G06T 7/37* (2017.01); *A61B 5/4064* (2013.01); *G06T 2207/30016* (2013.01)

(58) Field of Classification Search
CPC ............ A61B 2576/026; A61B 5/4064; A61B 5/7246; A61B 5/7253; A61B 5/7275;
(Continued)

(56) References Cited

U.S. PATENT DOCUMENTS

| | | |
|---|---|---|
| 8,155,452 B2 | 4/2012 | Minear |
| 2003/0228042 A1 | 12/2003 | Sinha |

(Continued)

FOREIGN PATENT DOCUMENTS

| | | |
|---|---|---|
| CN | 102200119 A | 9/2011 |
| RU | 2638761 C2 | 12/2017 |

OTHER PUBLICATIONS

Goshtasby, Arthur, "2-D and 3-D Image Registration: for Medical, Remote Sensing, and Industrial Application", Wiley, Mar. 2005.
(Continued)

*Primary Examiner* — Zhiyu Lu
(74) *Attorney, Agent, or Firm* — M&B IP Analysts, LLC

(57) ABSTRACT

A method and system for image-based region detection. Transformation matrices are computed by performing image registration between a target image and each of one or more reference images. Each transformation matrix is for transforming each of the reference images into a coordinate system of the target image. An optimal reference image is selected from among the reference images based on similarity measures between the target image and each reference image. The transformation matrix of the selected reference image is applied to a reference map associated with the reference image in order to generate a target map for the target image. The target map includes region labels indicating regions shown in the target image.

17 Claims, 5 Drawing Sheets

(51) Int. Cl.
*G06T 7/37* (2017.01)
*A61B 5/00* (2006.01)

(58) Field of Classification Search
CPC . G06T 2207/20128; G06T 2207/30016; G06T 7/0014; G06T 7/11; G06T 7/30; G06T 7/337; G06T 7/37
See application file for complete search history.

(56) References Cited

U.S. PATENT DOCUMENTS

| | | | |
|---|---|---|---|
| 2014/0247977 A1* | 9/2014 | Han | G06T 7/12 382/159 |
| 2015/0086096 A1* | 3/2015 | Liu | G06T 7/11 382/131 |
| 2017/0042622 A1 | 2/2017 | Yang et al. | |
| 2017/0220850 A1 | 8/2017 | Caprioli et al. | |
| 2017/0245940 A1 | 8/2017 | Piron et al. | |
| 2018/0185003 A1 | 7/2018 | Zou et al. | |
| 2019/0251694 A1* | 8/2019 | Han | G06T 7/11 |

OTHER PUBLICATIONS

Maddaiah, PN, et al., "Optimization of Image Registration for Medical Image Analysis", International Journal of Computer Science and Information Technologies, vol. 5 (3), 2014.
Razlighi, et. al., "Evaluating Similarity Measures for Brain Image Registration", J Vis Commun Image Represent, vol. 24, Oct. 2013, pp. 977-987.
International Search Report and Written Opinion of International Searching Authority for PCT/US2020/041959, ISA/RU, Moscow, Russia, dated: Oct. 19, 2020.

* cited by examiner

SYSTEM AND METHOD FOR REGION DETECTION IN TISSUE SECTIONS USING IMAGE REGISTRATION

CROSS-REFERENCE TO RELATED APPLICATIONS

This application claims the benefit of U.S. Provisional Patent Application No. 62/880,787 filed on Jul. 31, 2019, the contents of which are hereby incorporated by reference.

TECHNICAL FIELD

The present disclosure relates generally to region detection using image processing, and more specifically to automating detection of regions in tissue sections based on relative positions among images.

BACKGROUND

Large amounts of high-quality images showing portions of the brain are collected for research and diagnostic purposes. These images may be used for detecting early stages of diseases that manifest as mental decline. In particular, large numbers of imaged tissue sections are accumulated.

This high number of images present a tremendous opportunity for improving research and diagnoses. However, analyzing these images to extract meaningful insights has become a research bottleneck. Specifically, images of portions of the brain may show any of several discrete regions of interest of tissue sections. It is therefore desirable to extract readouts for these different regions separately.

In order to effectively analyze large sets of these images, existing solutions involve doctors or researchers manually labeling brain images with coordinates. In such solutions, a person observes an image and, based on his or her experience observing prior images of the brain and the appearance of different portions of the image, identifies each region. However, this manual labeling is time-consuming, subjective, and requires a person individually labeling each and every image with labels indicating specific regions. Further, this process is subject to human error, as any mislabeled sections result in a mislabeled image which detracts from the accuracy of analysis of the set.

It would therefore be advantageous to provide a solution that would overcome the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for image-based region detection. The method comprises: image-based region detection, comprising: computing a plurality of transformation matrices by performing image registration between a target image and each of a plurality of reference images, wherein each transformation matrix is a set of values for transforming one of the reference images into a coordinate system of the target image, wherein each reference image corresponds to a respective reference map; selecting an optimal reference image from among the plurality of reference images based on at least one similarity measure between the target image and each of the plurality of reference images; and generating a target map for the target image by applying the transformation matrix of the optimal reference image to the corresponding reference map of the optimal reference image.

Certain embodiments disclosed herein also include a non-transitory computer readable medium having stored thereon causing a processing circuitry to execute a process, the process comprising: computing a plurality of transformation matrices by performing image registration between a target image and each of a plurality of reference images, wherein each transformation matrix is a set of values for transforming one of the reference images into a coordinate system of the target image, wherein each reference image corresponds to a respective reference map; selecting an optimal reference image from among the plurality of reference images based on at least one similarity measure between the target image and each of the plurality of reference images; and generating a target map for the target image by applying the transformation matrix of the optimal reference image to the corresponding reference map of the optimal reference image.

Certain embodiments disclosed herein also include a system for image-based region detection. The system comprises: a processing circuitry; and a memory, the memory containing instructions that, when executed by the processing circuitry, configure the system to: compute a plurality of transformation matrices by performing image registration between a target image and each of a plurality of reference images, wherein each transformation matrix is a set of values for transforming one of the reference images into a coordinate system of the target image, wherein each reference image corresponds to a respective reference map; select an optimal reference image from among the plurality of reference images based on at least one similarity measure between the target image and each of the plurality of reference images; and generate a target map for the target image by applying the transformation matrix of the optimal reference image to the corresponding reference map of the optimal reference image.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
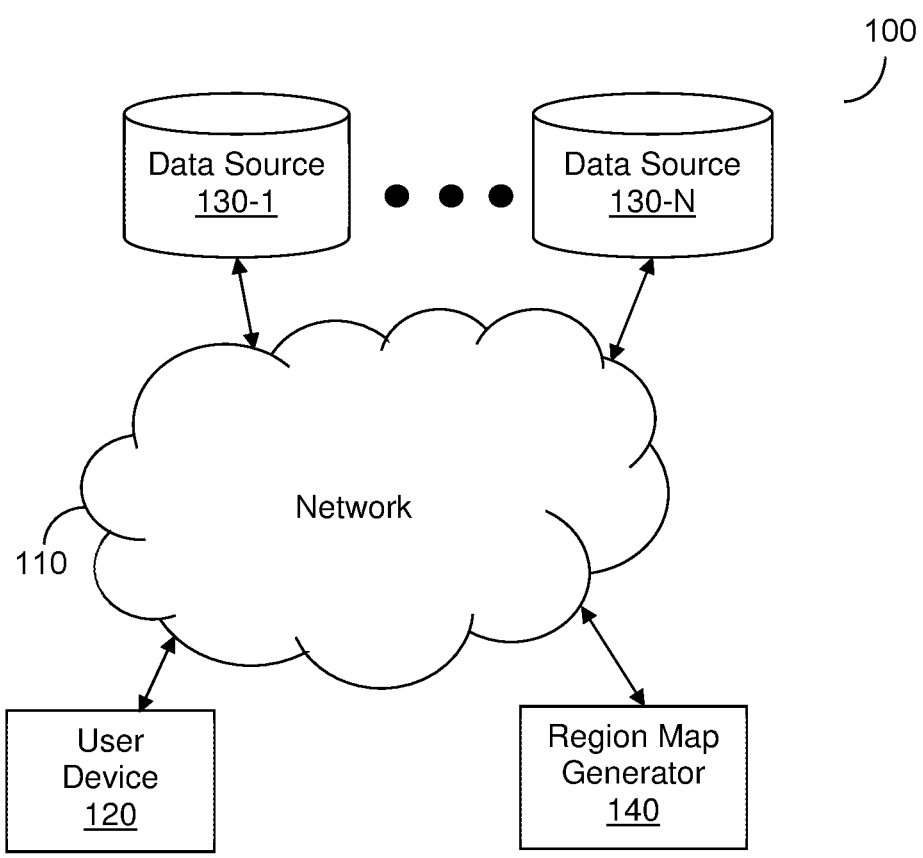
FIG. 1 is a network diagram utilized to describe various disclosed embodiments.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

It has been identified that image registration may be utilized to accurately map regions of the brain among different images and, therefore, to accurately identify tissue sections corresponding to these regions. More specifically, it has been identified that a transformation matrix used to transform different images to the same coordinate system may be applied to a map of brain regions shown in one of the images in order to create an accurate map of the same brain regions in the other image. It has been further identified that relative positions of images provide more accurate image registration with respect to brain images than using signal intensity.

The disclosed embodiments therefore provide an automated solution that utilizes a reference image having a pre-labeled reference map indicating regions of the brain shown therein in order to generate a target map including region labels for a target image. To this end, the disclosed embodiments provide techniques for processing images and transforming region label maps that allows for accurately mapping regions of the brain in target images.

The various disclosed embodiments include a method and system for image processing and for identifying tissue sections using processed images. One or more reference images are obtained. The reference images are images of one or more brain tissue samples captured at a specific orientation and each reference image is associated with a respective reference map providing labels indicating brain regions shown in its respective reference image. Image registration is performed on a target image with respect to each of the reference images. The target image is an image of a brain tissue sample captured at the same or approximately the same orientation as the reference images.

One of the reference images is selected based on the image registration. The selected reference image has an optimal registration with respect to the target image as determined based on one or more similarity measures. The transformation matrix used for image registration between the selected reference image and the target image is applied to the reference map associated with the selected reference image. The result is a target map that provides labels indicating the brain regions shown in the target image. In some implementations, the target map may be provided to a user (e.g., by displaying the target map overlaid on the target image) and user feedback may be utilized in order to improve subsequent iterations of the image processing.

The image processing according to the disclosed embodiments allows for automating identification of tissue sections while providing accuracy that is typically higher than solutions based on signal intensity. Application of an appropriate transformation matrix found using image registration therefore allows for automating region detection in a manner that is different than the manual labeling used by some existing solutions. In particular, maps for a limited number of reference images need to be manually labeled initially, and maps for subsequent target images may be generated without requiring additional manual labeling. In contrast, existing solutions either require manual labeling of all reference images or suffer from significantly lower accuracy than such manual labeling.

FIG. 1 shows an example network diagram 100 utilized to describe the various disclosed embodiments. In the example network diagram 100, a user device 120, data sources 130-1 through 130-N (hereinafter referred to individually as a data source 130 and collectively as data sources 130 for simplicity), and a region map generator 140 communicate via a network 110. The network 110 may be, but is not limited to, a wireless, cellular or wired network, a local area network (LAN), a wide area network (WAN), a metro area network (MAN), the Internet, the worldwide web (WWW), similar networks, and any combination thereof.

The user device (UD) 120 may be, but is not limited to, a personal computer, a laptop, a tablet computer, a smartphone, a wearable computing device, or any other device configured for receiving and displaying data such as images and region maps. In various implementations, the user device 120 may be configured to display a graphical user interface (GUI). The GUI may further allow for a user to interact with a displayed image using functions such as, but not limited to, zooming in, zooming out, dragging the image, looking at region labels corresponding to, manually adding or changing region labels, and the like.

The data sources 130 may include, but are not limited to, databases or other sources of image data and region maps. The data sources 130 at least store reference images and corresponding reference region maps to be used according to the various disclosed embodiments. The data sources 130 may further store target images and corresponding target maps generated according to the disclosed embodiments.

The reference maps include region labels for a number of regions. In an example implementation, the number of regions is between 3 and 20.

Figure 4A:
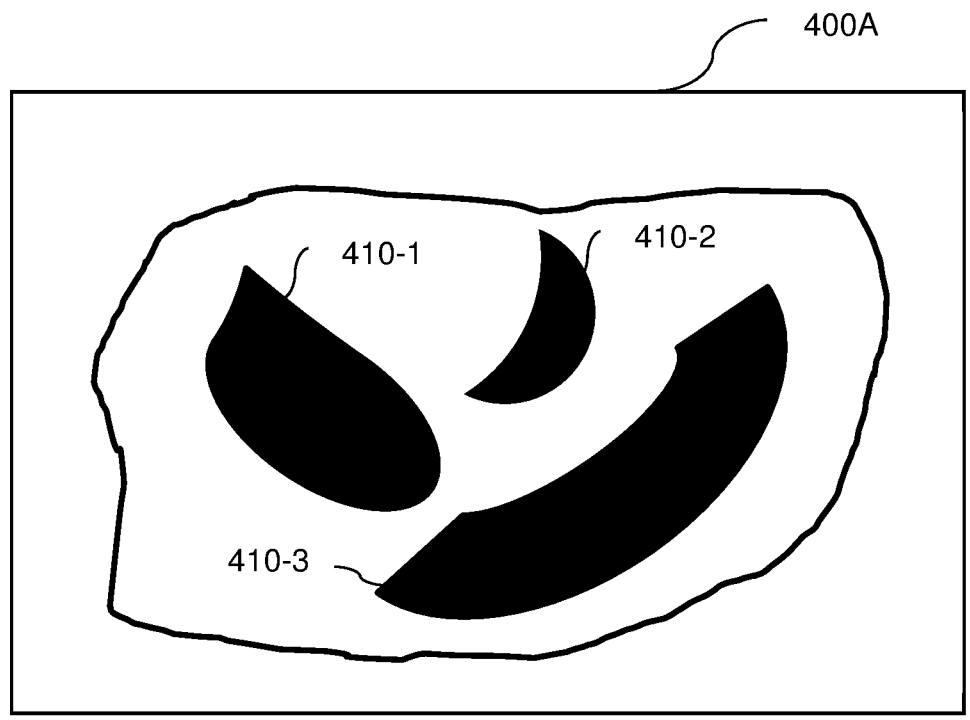
FIGS. 4A-B are example images showing an image and a map, respectively.
Figure 4B:
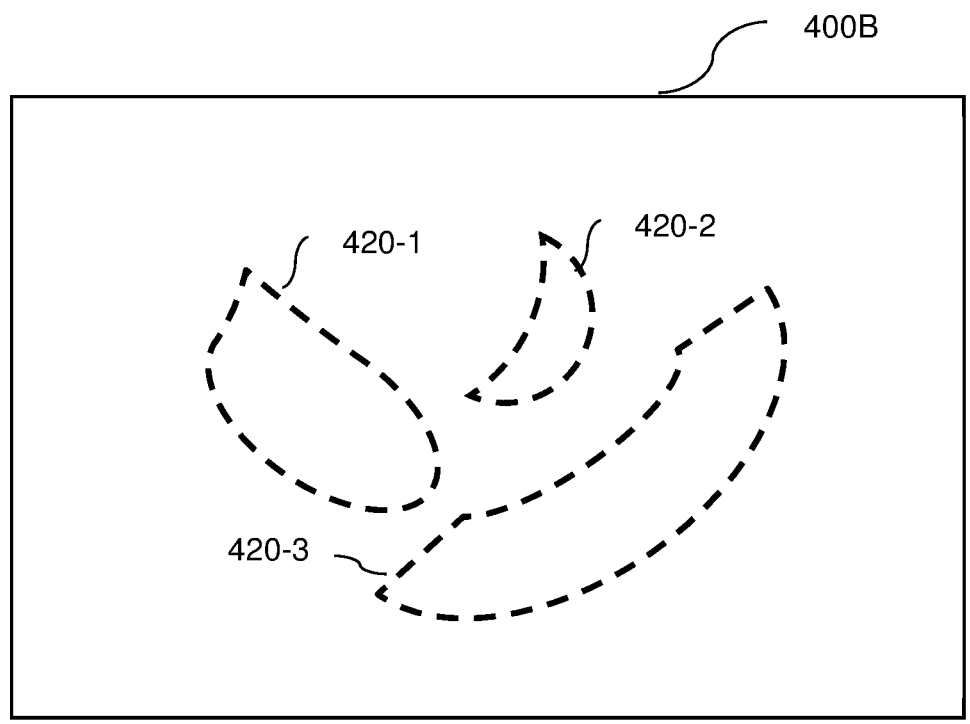

FIGS. 4A-B show an example image and an example corresponding map, respectively. In FIG. 4A, an example image 400A shows various regions 410-1 through 410-3. FIG. 4B is an example map 400B that is labeled with region labels 420-1 through 420-3. Each of the region labels 420 corresponds to a respective region 410 such that, in the examples shown in FIGS. 4A-B, the region label 420-1 corresponds to the region 410-1, the region label 420-2 corresponds to the region 410-2, and the region label 420-3 corresponds to the region 410-3. The map 400B may be a reference map that is manually labeled and used as an input to the image registration or may be a target map generated based on a transformation matrix as discussed herein.

Returning to FIG. 1, the region map generator 140 is configured to detect regions in brain images in accordance with the disclosed embodiments. To this end, the region map generator 140 may be configured to receive or retrieve reference images and maps from the data sources 130, to perform image registration between reference images and target images, and to apply transformation matrices found using such image registration to reference maps in order to generate target maps. The region map generator 140 may send the results of such processes (e.g., generated target maps along with their corresponding target images) to the user device 120 for review and feedback.

It should be noted that a network 110 is shown as being used for communications merely as an example, but that the network 110 may be optional in various implementations. In particular, the region map generator 140 may receive images to be processed from, for example, a local storage (not shown).

Figure 2:
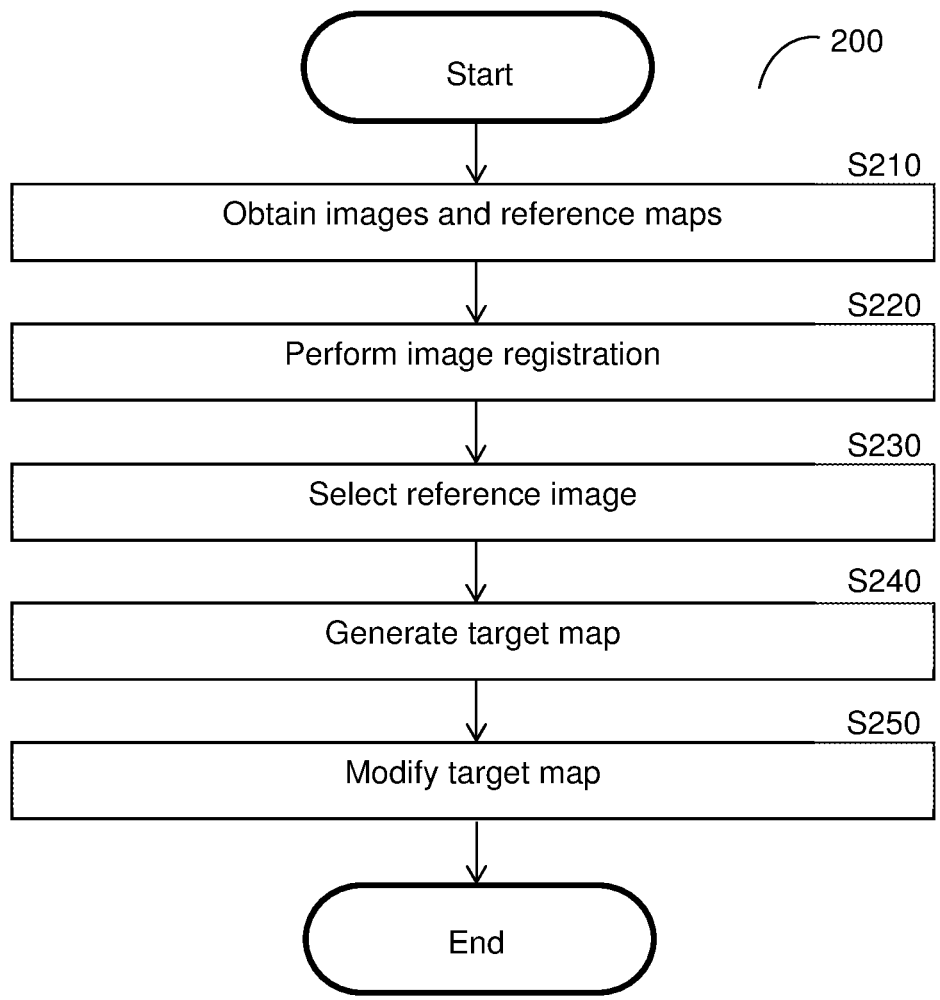
FIG. 2 is a flowchart illustrating a method for detecting regions using image registration according to an embodiment.

FIG. 2 is an example flowchart 200 illustrating a method for detecting regions using image registration according to an embodiment. In an embodiment, the method is performed by the region map generator 140, FIG. 1.

At S210, images and reference maps are obtained. Obtaining the images and reference maps may include, but is not limited to, receiving them, retrieving them, both, and the like. The images include one or more reference images and a target image. The reference maps include a reference map corresponding to each obtained reference image.

At S220, image registration is performed between each reference image and the target image. The image registration is a process for transforming the different images into a single coordinate system. The result of the image registration is a transformation matrix for each reference image used to relate the target image to the reference image. In an embodiment, the transformation matrix includes linear transformation models for rotation, translocation, scale, and shearing, respectively.

In an embodiment, S220 may include one or more optimizations. As non-limiting examples, S220 may include regular step gradient descent optimization, mean squares optimization, both, and the like.

At S230, one of the reference images is selected based on the image registration. The selected reference image is the image having the optimal image registration with respect to the target image. In an embodiment, the optimal image registration is determined based on values of one or more similarity measures. As a non-limiting example, the sum of squared differences between the target image and each reference image may be determined such that the reference image for which the sum of squared differences is lowest is selected as the reference image having the optimal image registration. It should be noted that other similarity measures may be used alternatively or collectively. Other example similarity measures include, but are not limited to, sum of absolute difference, correlation ratio, and the like.

More specifically, the selected reference image is an optimal reference image having a highest similarity as reflected in its respective similarity measures. As a non-limiting example, the reference with the lowest sum of squared difference has the highest similarity. As another non-limiting example, the reference with the highest correlation ratio has the highest similarity. When multiple similarity measures are used, each similarity measure may be assigned a weight, and a score representing a degree of similarity is determined for each similarity measure for each reference image. Thus, a weighted similarity score may be computed for each reference image by adding the weighted scores of similarity measures for each reference image and the reference image having the highest weighted similarity score is determined as having the highest similarity such that it is selected as the optimal reference image.

At S240, a target map is generated based on the reference map and the transformation matrix of the selected reference image. In an embodiment, S240 includes applying the transformation matrix of the selected reference image to the reference map. The result is a target map which is labeled with region labels indicating regions shown in the target image.

Figure 5:
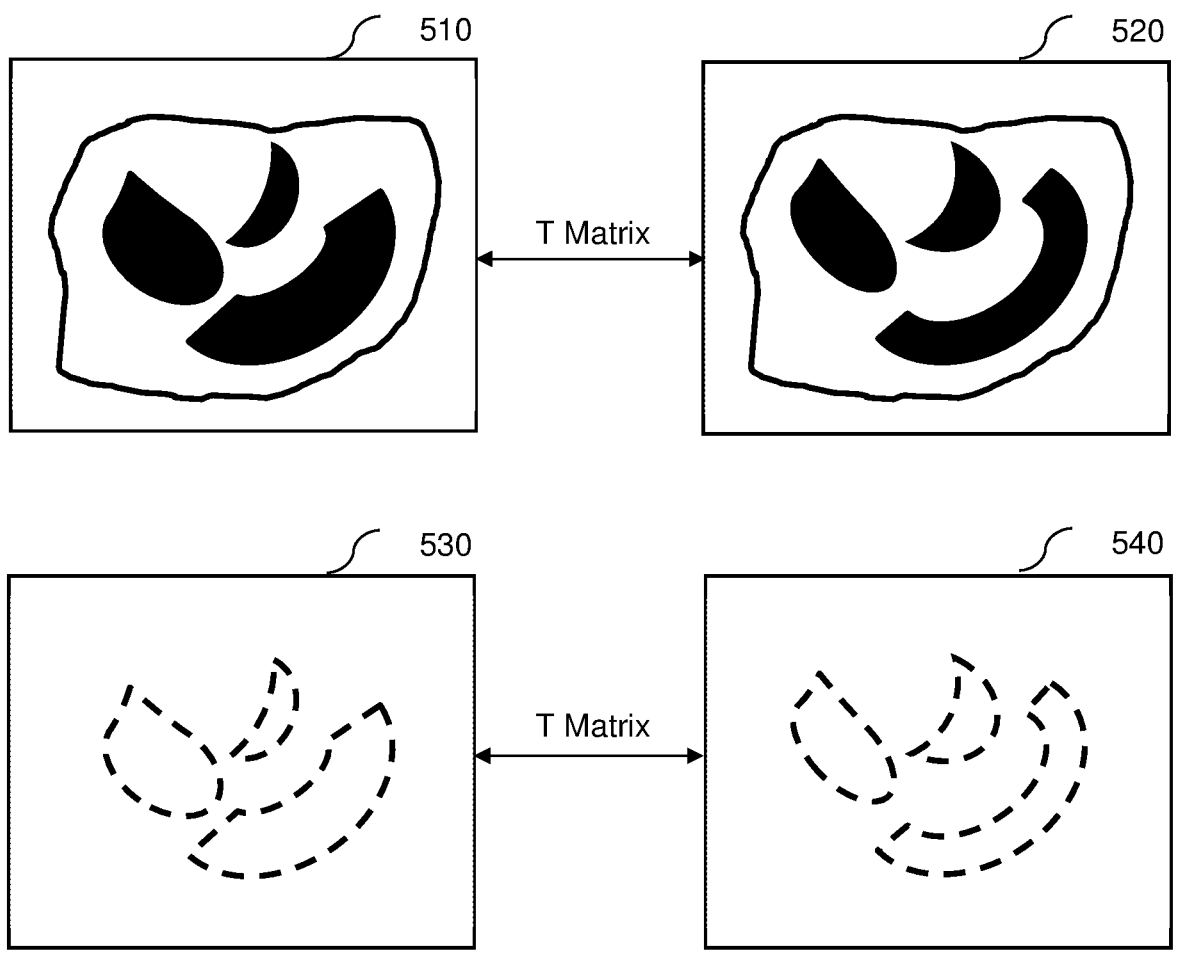
FIG. 5 is an example diagram utilized to describe relationships between images and corresponding maps according to an embodiment.

FIG. 5 is an example illustration demonstrating generation of a target map based on a transformation matrix used to transform a reference image into the same coordinate system as a target image. In FIG. 5, a transformation matrix ("T Matrix") can be used to convert a reference image 510 to a target image 520. The reference image 510 and the target image 520 are captured at the same or roughly the same orientation, and show different samples of brain (e.g., samples from different subjects). When the transformation matrix has been determined as described herein, it can be applied to a reference map 530 in order to transform the reference map 530, thereby creating a target map 540 corresponding to the target image 520.

Returning to FIG. 2, at optional S250, the generated target map is modified based on an evaluation of the target map and the target image. The modified target map may be stored along with its corresponding target image to be used in subsequent iterations as a reference map.

In an embodiment, S250 includes sending the target map and the target image to a user (e.g., by sending the map and image to a user device for display), and receiving the user feedback (e.g., based on inputs to a graphical user interface). Modifying the target map based on user feedback allows for improving future target map generation by providing more accurate reference maps.

In another embodiment, S250 includes performing an automated evaluation of the generated target map. In a further embodiment, the automated evaluation includes summing an intensity per region labeled by the target map and comparing the summed intensities of the regions to a sum of intensity for a background. The background is an area in the target image that shows a portion of the brain but does not belong to one of the labeled regions. Using intensities to perform such an evaluation of target maps as described herein allows for improving such target maps by providing an automated check for unusually low-intensity regions which may represent misidentified regions.

Figure 3:
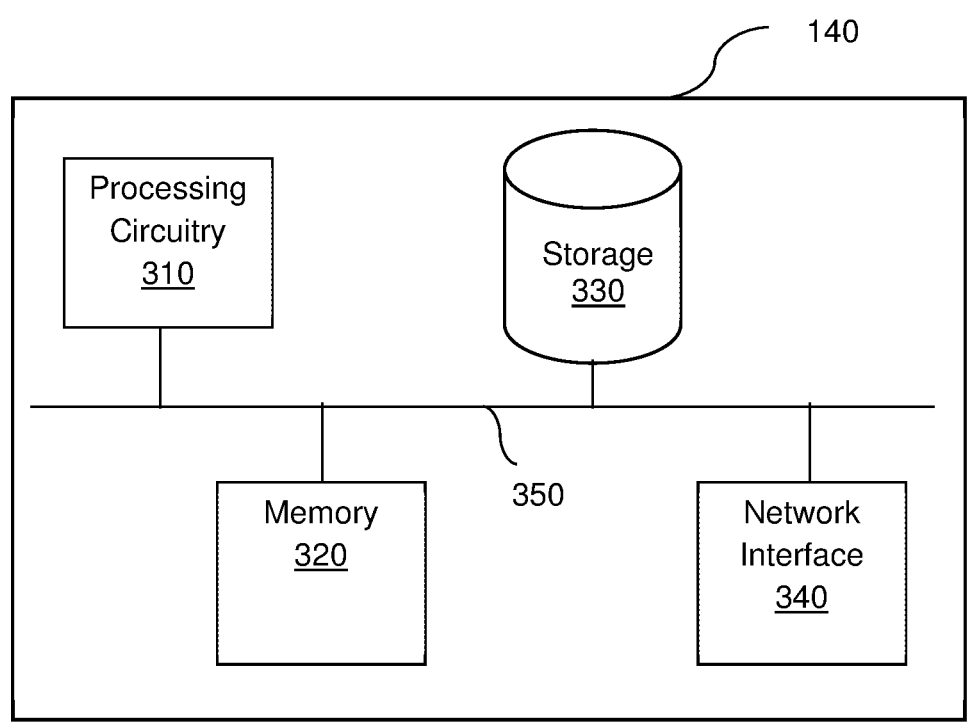
FIG. 3 is a schematic diagram of a region map generator according to an embodiment.

FIG. 3 is an example schematic diagram of a region map generator 140 according to an embodiment. The region map generator 140 includes a processing circuitry 310 coupled to a memory 320, a storage 330, and a network interface 340. In an embodiment, the components of the region map generator 140 may be communicatively connected via a bus 350.

The processing circuitry 310 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), general-purpose microprocessors, microcontrollers, digital signal processors (DSPs), and the like, or any other hardware logic components that can perform calculations or other manipulations of information.

The memory 320 may be volatile (e.g., RAM, etc.), non-volatile (e.g., ROM, flash memory, etc.), or a combination thereof. In one configuration, computer readable instructions to implement one or more embodiments disclosed herein may be stored in the storage 330.

In another embodiment, the memory 320 is configured to store software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 310, cause the processing circuitry 310 to perform the various processes described herein.

The storage 330 may be magnetic storage, optical storage, and the like, and may be realized, for example, as flash memory or other memory technology, CD-ROM, Digital Versatile Disks (DVDs), or any other medium which can be used to store the desired information.

The network interface 340 allows the region map generator 140 to communicate with the data sources 130 for the purpose of, for example, retrieving microscopic images for processing. Further, the network interface 340 allows the region map generator 140 to communicate with the user device 120 for the purpose of sending processed images.

It should be understood that the embodiments described herein are not limited to the specific architecture illustrated in FIG. 3, and other architectures may be equally used without departing from the scope of the disclosed embodiments.

It should be noted that various embodiments are described with respect to performing image registration with respect to images, but that other data which visually depicts tissues and can be transformed via image registration may be equally utilized. As a non-limiting example, such visual data may include frames of videos.

Additionally, it should be noted that the techniques disclosed herein may be applied to other visual data demonstrating discrete regions. Examples of other uses for the disclosed techniques may be facial recognition or identifying regions in other organs (e.g., kidneys).

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for image-based region detection, comprising:
computing a plurality of transformation matrices by performing image registration between a target image and each of a plurality of reference images, wherein each transformation matrix is a set of values for transforming one of the reference images into a coordinate system of the target image, wherein each reference image corresponds to a respective reference map;
selecting an optimal reference image from among the plurality of reference images based on at least one similarity measure between the target image and each of the plurality of reference images; and
generating a target map corresponding to the target image by applying the transformation matrix of the optimal reference image to the corresponding reference map of the optimal reference image, wherein the target map includes a plurality of region labels, each region label indicating a respective tissue region shown in the target image.

2. The method of claim 1, further comprising:
determining a similarity of each of the plurality of reference images based on the at least one similarity measure between the reference image and the target image, wherein the optimal reference image has the highest determined similarity among the plurality of reference images.

3. The method of claim 1, wherein each region label further indicates a plurality of intensities in the respective region, further comprising:
determining a region intensity of each tissue region by summing the plurality of intensities indicated by the region label of each tissue region;
comparing each region intensity to a sum of intensities for a background of the target image, wherein the background is an area in the target image that does not belong to any of the tissue regions indicated by the plurality of region labels; and
modifying the target map based on the comparison.

4. The method of claim 1, further comprising:
modifying the target map based on user feedback, wherein the user feedback is based on the target map and the target image.

5. The method of claim 1, wherein each of the plurality of reference images is an image showing a portion of a respective first tissue captured at a first orientation, wherein the target image is an image of a second tissue captured at a second orientation, wherein the second orientation is approximately the same as the first orientation.

6. The method of claim 1, wherein each transformation matrix includes a linear transformation model for each of rotation, translocation, scale, and shearing.

7. The method of claim 1, wherein computing each transformation matrix further comprises performing at least one of: regular step gradient descent optimization, and mean squares optimization.

8. The method of claim 1, wherein the at least one similarity measure includes at least one of: sum of squared difference, sum of absolute difference, and correlation ratio.

9. A non-transitory computer readable medium having stored thereon instructions for causing a processing circuitry to execute a process, the process comprising:
   computing a plurality of transformation matrices by performing image registration between a target image and each of a plurality of reference images, wherein each transformation matrix is a set of values for transforming one of the reference images into a coordinate system of the target image, wherein each reference image corresponds to a respective reference map;
   selecting an optimal reference image from among the plurality of reference images based on at least one similarity measure between the target image and each of the plurality of reference images; and
   generating a target map corresponding to the target image by applying the transformation matrix of the optimal reference image to the corresponding reference map of the optimal reference image, wherein the target map includes a plurality of region labels, each region label indicating a respective tissue region shown in the target image.

10. A system for image-based region detection, comprising:
    a processing circuitry; and
    a memory, the memory containing instructions that, when executed by the processing circuitry, configure the system to:
    compute a plurality of transformation matrices by performing image registration between a target image and each of a plurality of reference images, wherein each transformation matrix is a set of values for transforming one of the reference images into a coordinate system of the target image, wherein each reference image corresponds to a respective reference map;
    select an optimal reference image from among the plurality of reference images based on at least one similarity measure between the target image and each of the plurality of reference images; and
    generate a target map corresponding to the target image by applying the transformation matrix of the optimal reference image to the corresponding reference map of the optimal reference image, wherein the target map includes a plurality of region labels, each region label indicating a respective tissue region shown in the target image.

11. The system of claim 10, wherein the system is further configured to:
    determine a similarity of each of the plurality of reference images based on the at least one similarity measure between the reference image and the target image, wherein the optimal reference image has the highest determined similarity among the plurality of reference images.

12. The system of claim 10, wherein each region label further indicates a plurality of intensities in the respective region, wherein the system is further configured to:
    determine a region intensity of each tissue region by summing the plurality of intensities indicated by the region label of each tissue region;
    compare each region intensity to a sum of intensities for a background of the target image, wherein the background is an area in the target image that does not belong to any of the tissue regions indicated by the plurality of region labels; and
    modify the target map based on the comparison.

13. The system of claim 10, wherein the system is further configured to:
    modify the target map based on user feedback, wherein the user feedback is based on the target map and the target image.

14. The system of claim 10, wherein each of the plurality of reference images is an image showing a portion of a respective first tissue captured at a first orientation, wherein the target image is an image of a second tissue captured at a second orientation, wherein the second orientation is approximately the same as the first orientation.

15. The system of claim 10, wherein each transformation matrix includes a linear transformation model for each of rotation, translocation, scale, and shearing.

16. The system of claim 10, wherein computing each transformation matrix further comprises performing at least one of: regular step gradient descent optimization, and mean squares optimization.

17. The system of claim 10, wherein the at least one similarity measure includes at least one of: sum of squared difference, sum of absolute difference, and correlation ratio.

* * * * *